United States Patent [19]
Kloepper et al.

[11] Patent Number: 5,503,651
[45] Date of Patent: Apr. 2, 1996

[54] PLANT GROWTH-PROMOTING RHIZOBACTERIA FOR AGRONOMIC, NONROOT CROPS

[75] Inventors: Joseph Kloepper, Georgetown; Fran Scher, Bramalea, both of Canada

[73] Assignee: Cominco Fertilizers, Calgary, Canada

[21] Appl. No.: 438,739

[22] Filed: Jan. 31, 1995

Related U.S. Application Data

[63] Continuation of Ser. No. 898,042, Aug. 19, 1986, abandoned.

[51] Int. Cl.[6] .............................. C05F 11/08; H01R 4/10; A01C 1/06
[52] U.S. Cl. .............................. 71/6; 435/253.3; 435/850; 435/876; 435/877; 435/880; 47/57.6; 71/24
[58] Field of Search ................................. 71/1, 6, 7, 24; 435/253.3, 850, 876, 877, 880; 47/57.6

[56] References Cited

U.S. PATENT DOCUMENTS

| | | | |
|---|---|---|---|
| 4,465,017 | 8/1984 | Simmons | 47/Dig. 9 |
| 4,479,936 | 10/1984 | Vandebergh et al. | 424/93 |
| 4,584,274 | 4/1986 | Suslow | 47/58 X |

FOREIGN PATENT DOCUMENTS

| | | | |
|---|---|---|---|
| 671662 | 2/1963 | Canada | 71/6 |
| 1172585 | 8/1984 | Canada . | |
| 0064720 | 11/1982 | European Pat. Off. . | |
| 192342 | 8/1986 | European Pat. Off. . | |
| 227336 | 7/1987 | European Pat. Off. . | |
| 0027672 | 2/1985 | Japan | 71/7 |

OTHER PUBLICATIONS

D. M. Weller et al., "Suppression of Take-All of Wheat by Sead Treatment with Fluorescent Pseudomonads", Disease Control and Pest Management, vol. 73, No. 3, 1983, pp. 463–469. No month.

Peters, et al., Soil Science, "Effect of Legume Exudates on the Root Nodule Bacteria", vol. 102, No. 5, pp. 380–387, (1966). No month.

Suslow, et al., The American Phytopathological Society, "Rhizobacteria of Sugar Beets: Effects of Seed Application and Root Colonization on Yield", vol. 72, No. 2, pp. 199–206, (1982) No month.

Howell, et al., Phytopathology, "Control of Rhizoctonia solani on cotton seedlings with Pseudomonas fluorescens and with an antibiotic produced by the bacterium", 69, pp. 480–482, (1979) No month.

Kloepper, et al., Phytopathology, "Effects of Rhizosphere Colonization by Plant Growth–Promoting Rhizobacteria on Potato Plant Development and Yield", 70, pp. 1078–1082, (1980). No month.

Translation of Russian article, "Influence of soil microorganisms on virulence and activity of nodule forming bacteria", (and Russian article). No Date.

John Davison, Bio/Technology, "Plant Beneficial Bacteria", vol. 6, Mar. 1988, pp. 282–286.

A. Hussain et al., Folia Microbiol. (Prague), "Formation of Biologically Active Substance by Rhizophere Bacteria and their Effect on Plant Growth", 1970, 15(6), pp. 468–478 No month.

Chemical Abstracts, vol. 81, No. 11, Sep. 16, 1974, p. 231, Ab.No.60637v.

Chemical Abstracts, vol. 89, No. 11, Sep. 11, 1978, p. 256, Ab.No.87260u.

Chemical Abstracts, vol. 77, No. 9, Aug. 28, 1972, p. 123, Ab.No.57484e.

European Search Report.

N. Sakthivel, et al., IRRN, "Bacterization of rice with Pseudomonas fluorescens reduces sheath rot (ShR) infection", 11:3 (Jun. 1986), pp. 17–19.

(List continued on next page.)

Primary Examiner—Ferris Lander
Attorney, Agent, or Firm—Fitzpatrick, Cella, Harper & Scinto

[57] ABSTRACT

Bacterial strains can be reproducibly isolated from the rhizosphere that enhance yield in nonroot crops under field conditions.

46 Claims, 6 Drawing Sheets

OTHER PUBLICATIONS

D. M. Weller, et al., *Canadian Journal of Plant Pathology*, "Increased growth of wheat by seed treatments with fluorescent pseudomonads, and implications of Pythium control", 1986, No month, vol. 8(3), 228–334.

Kloepper et al, "Plant Growth Promoting Rhizobacteria on Radishes" in Proc.4th Int.Conf.Plant Path.Bact.Angers 879–82 (1978). No month.

Burr et al, "Increased Potato Yields by Treatment of Seed Pieces with Specific Strains . . . " Phytopathology 68: 1377–83 (1979) No month.

Kloepper et al, "Effects of Rhizosphere Colonization . . . " Phytopathologyl, 70: 1078–82 (1980). No month.

Kloepper et al, "Enhanced Plant Growth by Siderophores Produced by Plant Growth–Promoting Rhizobacteria" *Nature* 286:885–86 (1980) No month.

Suslow et al, "Rhizobacteria of Sugar Beets: Effects of Seed Application . . . " *Phytopathology,* 72: 199–206 (1982). No Month.

Caeser and Burr, "Growth Promotion of Apple Rootstocks by Rhizobacteria," *Phytopathol,* 75(11): 1290–91, (1985). No Month.

Scher et al, "A Method for Assessing the Root–Colonizing Capacity of Bacteria on Maize" *Can J. Microbiol,* 30: 151–57, (1984). No Month.

Schroth et al, *Science*, "Disease–Suppressive Soil and Root–Colonizing Bacteria" vol. 216, pp. 1376–1381, Jun. (1982).

Olsen et al, *Plant and Soil* "Responses of guayule seedlings to plant growth promoting fluorescent pseudomonads" (1984),77:97–101. No month.

PLANT GROWTH-PROMOTING RHIZOBACTERIA FOR AGRONOMIC, NONROOT CROPS

This application is a continuation of application Ser. No. 06/898,042 filed Aug. 19, 1986, now abandoned.

BACKGROUND OF THE INVENTION

An influence on plant growth by various strains of bacteria derived from the root zones of plants (the "rhizosphere") has been documented in several crops, including radish, potato and sugar beet. Both positive and negative growth effects mediated by rhizobacteria have been observed. Of particular interest are the plant growth-promoting rhizobacteria (PGPR), which are known to enhance plant growth in the aforementioned tuber plants, as well as in apple rootstocks, under field conditions. The following literature citations, which are hereby incorporated by reference, provide background information on known rhizobacterial effects on plant growth:

- Kloepper & Schroth, "Plant Growth Promoting Rhizobacteria on Radishes," in *PROC. 4th INT. CONF. PLANT PATH. BACT. ANGERS* 879–82 (1978).
- Burr et al, "Increased Potato Yields by Treatment of Seed Pieces With Specific Strains of *Pseudomonas fluorescens* and *P. putida*," Phytopathology 68:1377–83 (1979).
- Kloepper et al, "Effects of Rhizosphere Colonization by Plant Growth-Promoting Rhizobacteria on Potato Plant Development and Yield," *Phytopathology* 70: 1078–82 (1980a).
- Kloepper et al, "Enhanced Plant Growth by Siderophores Produced by Plant Growth-Promoting Rhizobacteria," *Nature* 286: 885–86 (1980b).
- Suslow & Schroth, "Rhizobacteria on Sugar Beets: Effects of Seed Application and Root Colonization on Yield," *Phytopathology* 72: 199–206 (1982).
- Olsen & Misaghi, "Responses of Guayule (*Parthenium argentatum*) Seedlings to Plant Growth Promoting Fluorescent Pseudomonads," *Plant and Soil* 77: 97–101 (1984).
- Caesar & Burr, "Growth Promotion of Apple Rootstocks by Rhizobacteria," *Phytopathol.* 75(11): 1290–91 (1985).

It is still unclear by what range of mechanisms PGPR increase plant growth. Work by Kloepper et al (1980b) on the role of microbial iron transport agents (siderophores) in the rhizosphere indicates one mechanism by which some fluorescent pseudomonad PGPR promote plant growth, i.e., by antagonism to potentially deleterious, indigenous fungi and bacteria. In this vein, it has been proposed that rhizobacteria-mediated enhancement of plant growth generally involves interactions of PGPR with rhizosphere microflora, possibly leading to the displacement of microorganisms detrimental to plant growth. For example, Canadian patent No. 1,172,585 discloses the use of particular strains of naturally-occurring pseudomonads to benefit plant growth in root crops by reducing the population of other indigenous root-zone microflora that adversely influence plant growth. Another hypothesis is that the PGPR elaborate substances that directly stimulate plant growth, such as nitrogen, hormones and compounds promoting the mineralization of phosphates.

The cited Canadian patent also illustrates the fact that the impact on growth of known PGPR strains is restricted largely to roots; hence, documented improvements in yield per se (as distinguished, for example, from simple root elongation) have been in root crops like radish, sugar beet and potato. In other agronomic crops, where an effect of root growth cannot be directly correlated with increased yield, there have been no reports of yield-related effects by PGPR. In the rubber-producing desert shrub called guayule, for example, PGPR-mediated increases in shoot weight, but not in seed yield, have been reported. In contrast, no rhizobacterial strains have been identified heretofore that enhance seed (grain) yield in any cereal or oilseed crop, or in maize.

SUMMARY OF THE INVENTION

It is therefore an object of the present invention to provide a category of PGPR strains, readily isolatable from root zones of plants in diverse habitats, that promote yield under field conditions of cereals (wheat, barley, oats, sorghum, rye, millet and rice), of the oilseed crops (soybean, flax and rapeseed, i.e., *Brassica napus* and *Brassica campestris*), maize, and of legumes.

It is also an object of the present invention to provide bacterial formulations, based on associative microorganisms naturally occurring in the rhizosphere, that are particularly effective in stimulating growth in the aforesaid crops.

In accomplishing the foregoing objects, there has been provided, in accordance with one aspect of the present invention, a bacterial culture consisting essentially of at least one rhizobacterial strain that increases yield in cereal, oilseed or maize plants. In a preferred embodiment, the culture of the present invention consists essentially of a rhizobacterial strain that also increases vigor and/or emergence rate in such plants.

In accordance with another aspect of the present invention, a composition of matter has been provided that comprises (i) at least one of the above-mentioned bacterial strains and (ii) an agriculturally compatible carrier, such as water or a water-based solution. In one preferred embodiment, the yield-promoting rhizobacterial strain(s) used in the composition are from at least one species of the group consisting of *Pseudomonas putida*, *Pseudomonas fluorescens*, *Arthrobacter citreus*, *Serratia liquefaciens* and *Flavobacterium* sp.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Figure 1A:
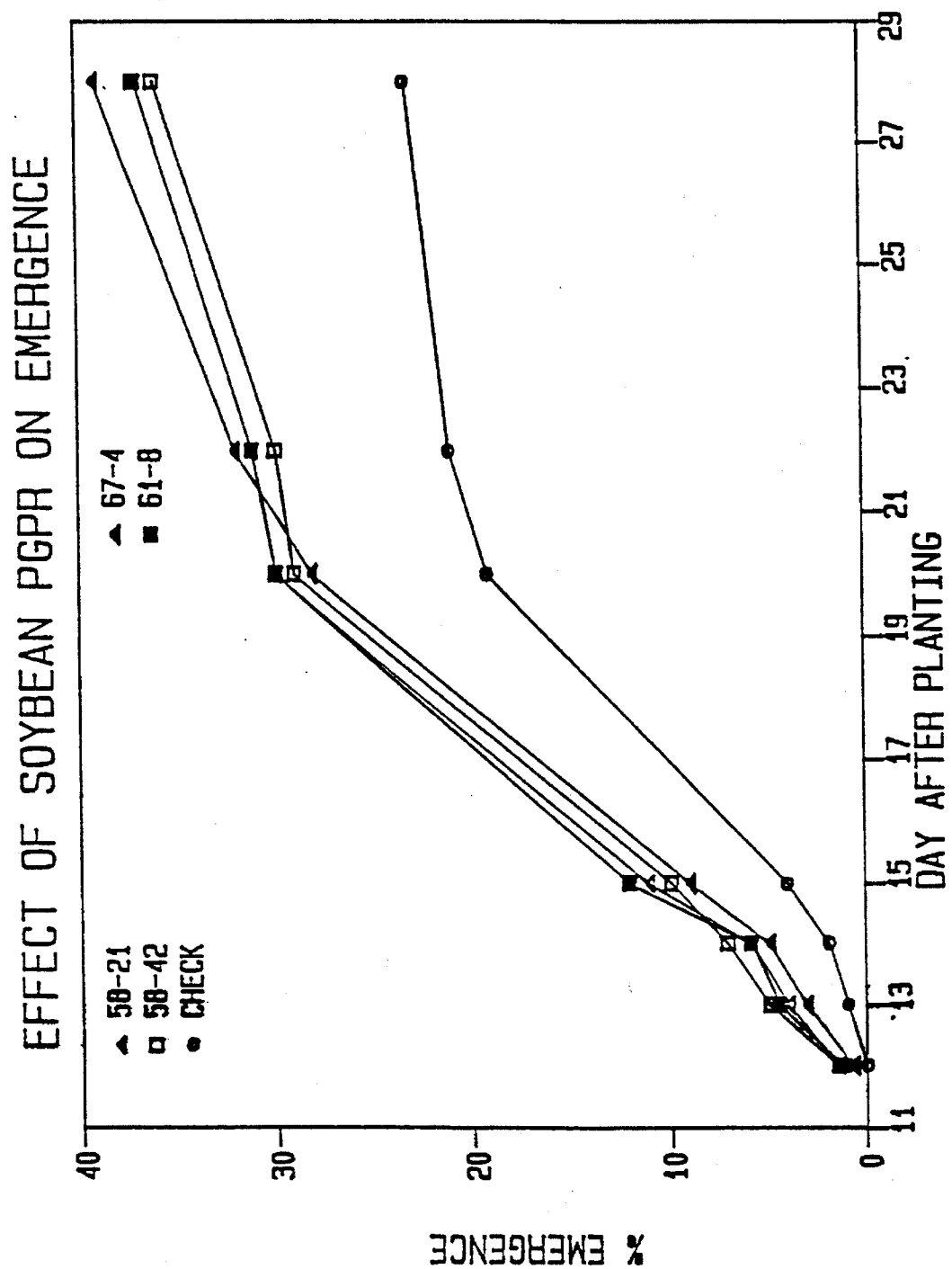
FIGS. 1A, 1B and 1C are graphs showing the effects of PGPR strains of the present invention on emergence (A), vigor (B) and yield (C) of soybean.

It has been discovered that the rhizosphere in a wide variety of habitats can be tapped, via known selection techniques, as the source for a class of PGPR that, surprisingly, enhance yield (as measured by seed production) in agronomic, nonroot crops. For purposes of the present description, the term "rhizosphere" is used interchangeably with "root zone" to denote that segment of the soil that surrounds and is influenced by the roots of a plant. (In this context, no distinction is drawn between "rhizosphere" and terminology which is more specific locationally, such as "rhizoplane.") Extensive selections from over 8000 bacterial strains collected from the root zones of native plants in a variety of eastern Canadian habitats have shown that a small but reproducible percentage of the total rhizobacterial population is characterized by an ability to stimulate yield in at least one of the above-mentioned crops.

Selection of naturally-occurring strains for use in the present invention starts with the collection of root-associated soil and/or root segments, from which sample dilutions are derived, as described below, for plating and incubation on a suitable nutrient medium. The initially isolated strains are individually screened for both chemotactic and root-colonization capacities and, optionally, for Gram-stain reaction. Other, more specialized characteristics, such as the ability to grow under specific conditions of temperature, soil-moisture content, pH and the like, can also be taken into consideration in screening the isolated strains. Thus, bacterial strains selected from the rhizosphere for use according to the present invention can also be screened for growth at 4° to 14° C., making them potentially effective in stimulating yield in early-spring cultivars of rapeseed and/or soybean.

The root-colonization capacity of an isolated strain can be gauged, for example, via a closed test tube assay which is based on the capacity of a bacterial strain to colonize the surface of roots when applied as a seed inoculum, as described by Scher et al, "A Method for Assessing the Root-Colonizing Capacity of Bacteria on Maize," *Can. J. Microbiol.* 30: 151–57 (1984), the contents of which are hereby incorporated by reference.

The relative root-colonization capacity of an isolated strain is also correlated with measured relative chemotactic capacity. Chemotactic capacity can be assayed by incubating the test strain on a soft agar medium containing an amino acid typically present in root exudates, such as asparagine or serine. Cultures grown in the presence of such an amino acid are examined to detect the presence of chemotactic zones, which are identified as areas of the agar medium that have become clouded by bacterial cells which have moved out from the inoculation zone. Thus, a soil or root sample containing putative PGPR is laid on the soft agar medium, and chemotactic zones resulting from bacteria migrating from the sample out toward the amino-acid attractant are then removed and plated separately.

As previously indicated, the initial identification of potential PGPR strains for use in the present invention can also include Gram-stain testing. Those skilled in the art have assumed heretofore that PGPR are generally Gram-negative. In fact, yield-enhancing rhizobacterial strains suitable for the present invention are typically Gram-negative; but it has also been discovered that selected strains testing positive for the ability to stimulate yield in soybean or rapeseed, as described below, can be Gram-positive or even "Gram-variable," in the sense that the same strain may test out Gram-positive at one time and Gram-negative another time.

For selected strains that show promise based on the results of chemotactic and root-colonization assays, further tests to establish genus can be conducted, including one or more of the following biochemical tests recommended by the American Society for Microbiology (ASM) in the MANUAL OF METHODS FOR GENERAL BACTERIOLOGY J24 (P. Gerhardt ed. 1981):

For confirmed Gram-negative strains— reaction profiles on API 20E test strips (product of Ayerst Labs, Inc., Plainview N.Y.); growth on MacConkey medium; type of metabolism in OF glucose medium; production of DNAase; fluorescent pigment production; gelatin hydrolysis; nitrate reduction; starch hydrolysis; oxidase reaction; and lipase production (Tween 80 hydrolysis); urease production and motility.

For confirmed Gram-positive strains— growth on MacConkey medium; type of metabolism in OF glucose medium; catalase test; gelatin hydrolysis; Voges-Proskauer reaction; indole production; citrate utilization; motility; urease production; endospore formation; and acid production from glucose, saccharose or mannitol.

Those isolated strains that display both chemotactic and root-colonizing capabilities and, preferably, Gram-negativity can be tested under greenhouse conditions for growth-promoting activity. Such activity is reflected, for example, in increases in root area or in leaf area. In this context, the index of increased root area has proved suitable for soybean. Leaf area is typically an appropriate indicium of growth-promotion in rape because assaying root area can be difficult in rapeseed plants, which commonly develop very fine, extended root systems. It is generally suitable, however, to measure shoot and root dry weight in order to assess growth-promoting activity under greenhouse conditions for the above-mentioned crops.

Selected strains testing positive in a greenhouse assay, as described above, can then be tested for growth promotion (and, more particularly, for yield enhancement) under field conditions in one or more of the above-mentioned nonroot crops. Alternatively, the intermediate stage of testing under greenhouse conditions can be omitted. For both greenhouse and field testing, in any event, the tested seed is preferably exposed to the putative PGPR strain(s) by dipping the seed into a liquid bacterial suspension, preferably water-based, and then is hand-planted. It has been found that this approach introduces the least amount of variability into the testing paradigm, making it easier to determine the repeatability of the growth-promotion response, particularly in field tests.

Alternatively, field testing can employ mechanically-planted seed, and other seed inoculant systems can be used, such as fine-ground peat containing a selected strain. Empirical evidence indicates, however, that peat-treated trials are often skewed by a negative effect of the peat itself on yield in controls (no bacterial exposure), particularly in rapeseed, a factor militating against the use of a peat inoculant for testing purposes.

As noted above, cultures of rhizobacterial strains within the present invention are initially isolated from soil or root samples by a conventional serial-dilutions technique which yields a "biologically pure" culture, i.e., one in which virtually all the bacterial cells present are of the selected strain. A biologically pure culture, thus defined, is a preferred embodiment of the present invention. Such a culture can be stored at −80° C. in glycerol, transferred to a bacteriological growing medium, incubated 1–2 days, centrifuged and mixed with water or buffer solution to create a PGPR suspension for seed treatments. A biologically pure culture of the present invention can also be lyophilized and stored until a bacterial suspension of the selected strain is reconstituted by the addition of a suitable liquid carrier, such as oil, to the lyophilized culture. In any event, a culture of a rhizobacterial strain within the present invention can contain microorganisms that do not interfere with the yield-promoting action of the cultured strain.

For practical applications of strains of the present invention in agriculture, liquid bacterial suspensions of the sort described above are preferably employed. Thus, an agricultural composition comprising one or more rhizobacterial strains that increase yield in cereal, oilseed or maize plants are preferably dispersed in a liquid carrier, which is preferably an aqueous solution or water. For example, an aqueous solution of $MgSO_4$ (usually around 0.1M) can be used as a carrier to enhance bacterial viability over time. Alternatively, a buffer solution can be used as the liquid carrier. An aqueous bacterial suspension of the present invention can also contain alginate or a similar polysaccharide-containing material in sufficient amounts (typically about 1% by weight) to convert the aqueous suspension into a slurry. Optionally, an agriculturally-compatible oil (as defined below) can be added to the slurry to create an emulsion in which rhizobacterial cells of the selected yield-enhancing strain(s) are dispersed.

Bacteria-containing compositions within the present invention can also be based on an agriculturally-compatible oil medium in which a selected strain is dispersed. In this context, the phrase "agriculturally-compatible" denotes a substance that can be used routinely under field conditions without adversely influencing crop development or the desired ecological balance in a cultivated area. Commercially available oils of this sort include mineral oil and vegetable oils, for example, soya oil, canola (rapeseed) oil and corn oil. An oil-based carrier can be mixed with a xanthan gum or similar, agriculturally-compatible gum to produce a bacterial emulsion.

When a liquid carrier is employed according to the present invention, the resulting rhizobacteria-containing composition can be mixed with rape or soybean seed or sprayed directly onto a field previously prepared for planting. Alternatively, a liquid bacterial suspension of the present invention can be absorbed into a granular carrier, such as pelleted peat or perlite granules, which is planted with the seed. Another alternative is to air-dry a liquid bacterial suspension of the present invention, at a temperature (typical range: 10°–30° C.) that is sufficiently low as not adversely to affect viability of the bacterial cells, to form a powder. The bacteria-containing powder can then be mixed with oil or another suitable liquid carrier, or with a dry carrier like peat, talc or diatomaceous earth.

The present invention will be further described by reference to the following illustrative examples.

EXAMPLE 1.

Selection of Rhizobacterial Strains.

Root-zone soils from 27 sites, and roots from 300 native plants from 25 other sites, were collected from diverse habitats in eastern Canada. Following Scher et al (1985), five-gram soil samples were mixed with 100 ml of seed exudate broth (30% exudate broth for rapeseed and 10% for soybean). After a 10-day incubation at 4° C. (agitation at 50 rpm), broth dilutions were made onto nutrient agar and Pseudomonas Agar F ("PAF"; product of Difco Labs, Detroit Mich.). The plates were incubated thereafter for 7 to 10 days at 4° C., and the fastest growing strains were purified for storage at –80° C. in 50% glycerol.

The roots that had been collected were cut into segments, each 2 to 5 cm in length, which were shaken vigorously is sterile 0.1M aqueous $MgSO_4$ solution; the root segments were then placed on asparagine soft agar (ASA), which contained 1 g L-asparagine, 2g Bacto Agar (product of Difco Labs, Detroit Mich.) and 1000 ml of distilled water. The ASA plates bearing the root segments were incubated at 14° C. and 28° C., and were examined daily for the presence of chemotactic zones. Agar at the edge of the chemotactic zones was mixed with 0.1M $MgSO_4$ and plated onto PAF. The resulting colonies were purified and stored at –80° C. in 50% glycerol.

The rhizobacterial strains thus isolated were tested for Gram-stain reaction, and those initially identified as Gram-negative were tested for rapid growth at 4°, 10° and 14° C. Strains that grew to an observable lawn within 24 hours at 14° C., 48 hours at 10° C., and 4–5 days at 4° C., respectively, were then tested for growth on exudate agar at 20° C. Exudate agar was prepared by mixing 10% soybean or 20% rapeseed exudates with 2% purified agar (Difco Labs) which had been washed three times with distilled water and dried. Seed exudates were prepared, as described by Scher et al (1985), using cv 'Maple Arrow' for soybean and cv 'Tobin' for rapeseed.

The bacterial strains pretested in this manner were stored at –80° C. in 50% glycerol before being tested in greenhouse assays described below. Strains that showed promise as PGPR in early tests, i.e., by growth-promotion activity in the greenhouse, were rechecked for purity on PAF, and 10 copies of each strain were returned to –80° C. storage. A new vial of bacteria was used for each subsequent greenhouse or field test described below.

Strains selected in accordance with the above-described regimen were identified to genus by the previously mentioned, ASM-recommended biochemical tests. The identification of PGPR strains are listed in Table 1.

TABLE 1

| IDENTIFICATION OF PGPR STRAINS | |
|---|---|
| Strain | Strain No. |
| Pseudomonas putida | 31-34, 63-36, G3-9 |
| | 25-71, 56-13, 54-26 |
| | 17-114, 55-13A, 55-14*, G23-34, 61-9A |
| Pseudomonas putida biovar B | 25-33 |
| Pseudomonas fluorescens | 63-49, 54-4 |
| | 39-8, 31-12, 34-36 |
| | 31-44, 63-28, 63-14 |
| | 61-16, 37-8, G8-17 |
| | 34-13, 55-13B, X, 62-24, 37-9, 46-8, |
| | 58-42, G2-52, 58-21, 61-8, 56-20, 67-4, |
| | G25-25, 57-10 |
| Arthrobacter citreus | 44-9 |
| Serratia liquefaciens | 1-141, 2-16 |
| Flavobacterium sp. (typed by ATCC) | G1-5 |

*Deposited with the American Type Culture Collection (Rockville MD) on August 15, 1986, under accession No. 53,530.

EXAMPLE 2.

Greenhouse Assays Using Selected Rhizobacterial Strains.

Both the rapeseed and the soybean PGPR assays were conducted in a 1:1 mix of perlite and field soil. Field soil was collected near Caledon, Ontario, and was a clay loam [2% organic matter, pH 7.0, total exchange capacity (M.E.) 14] with the following nutrient levels in ppm: nitrate nitrogen 4; phosphorous 1; potassium 2; calcium 70; magnesium 16; sodium 05; boron 0.4; iron 550; manganese 130; copper 2; and zinc 7.

Test bacteria were grown on PAF plates at 10° C. for 3 days (rapeseed assay) or at 28° C. for 48 hours (soybean assay), and then were scraped off the plates and mixed in 0.1M MgSO$_4$. Seeds were agitated in the bacterial suspensions for 2 hours at 10° C. (rapeseed) or for 1 hour at 20° C. (soybean). Control seeds were soaked in 0.1M MgSO$_4$ which had been poured over an uninoculated PAF plate. For both soybean and rapeseed, two seeds were planted per replication—a 7.5 cm square plastic pot for rapeseed and a 10 cm pot for soybean—and 6 replications were used per treatment. Rapeseed pots were placed at 10° C. for one week before being placed in a greenhouse with day/night temperatures of 22°/15° C. Soybean pots were immediately placed in a greenhouse with day/night temperatures of 30°/25° C. Seedlings of both plant types were thinned to one per pot after emergence.

Rapeseed plants from bacterial treatments were checked after three to four weeks (prior to bolting) for increases in leaf area relative to control plants. The plants were rated from 0 to 3, where 0= no increase compared to control, 1= some increase with some reps, 2= obvious consistent increase, 3= very great increase in leaf area. Soybean plants were examined, after washing of the root systems, for root area increases at the first trifoliate leaf stage; the same 0–3 rating system was used to compare bacterial treatments with controls.

Bacterial strains that induced increased plant growth in either the rapeseed or the soybean assays at a level of 2 or 3 in the first test were retested at least twice. Most strains that induced a rating of 2 in two of three repeating tests were subsequently retested two more times (Tables 2 and 3). The emphasis in the greenhouse assays, which were continually conducted over a two-year period, was on repeatability of the growth promotion response.

Among over 8000 rhizobacterial strains isolated as described in Example 1, a total of 887 strains were tested in the rapeseed greenhouse assay, and 222 of these induced increases in leaf area compared to controls, with a rating of 2 or 3 in the first test. Of these 222 strains, 35 induced growth promotion in at least two of the first three tests (see Table 2). Some of the strains were tested a total of ten or eleven times, with frequencies of growth promotion (rating 2 or 3) as great as 8/11 for 2 strains, 7/11 for 2 strains, 7/10 for 3 strains, and 8/9 for 1 strain (Table 2).

In the soybean assay, 62 of 310 tested strains induced root mass increases, compared to controls, with a rating of 2 or 3 in the first test. Nineteen strains induced growth promotion in at least 2 of the first 3 tests (see Table 3). Most of those strains were screened in a total of five tests, and some were screened in eight tests with frequencies of growth promotion as great as 7/8 for 1 strain, 6/8 for 2 strains, 5/6 for 1 strain and 4/5 for 2 strains (Table 3 ).

TABLE 2

SUMMARY OF GREENHOUSE ASSAYS FOR SELECTION OF RAPESEED PGPR

| Strain | Score[1] Trial # | | | | | | | | | | | No. Trials With Score 2 or 3/ Total No. Trials |
|---|---|---|---|---|---|---|---|---|---|---|---|---|
| | 1 | 2 | 3 | 4 | 5 | 6 | 7 | 8 | 9 | 10 | 11 | |
| 63-09 | 2 | 2 | 0 | 2 | — | — | — | — | — | — | — | 3/4 |
| 65-06 | 2 | 1 | 2 | 1 | 0 | — | — | — | — | — | — | 2/5 |
| 44-9 | 2 | 1 | 2 | 2 | 0 | 2 | 2 | 2 | 0 | 2 | 2 | 8/11 |
| 36-43 | 2 | 2 | 1 | 2 | 1 | 2 | 1 | 1 | 1 | — | — | 4/9 |
| 36-44 | 2 | 2 | 1 | 2 | 1 | 1 | 2 | 2 | 1 | 0 | — | 5/10 |
| 31-12 | 2 | 2 | 2 | 2 | 0 | 1 | 0 | 0 | 1 | — | — | 4/9 |
| 34-13 | 2 | 2 | 1 | 1 | 2 | 2 | 2 | 1 | 1 | 2 | — | 6/10 |
| 31-34 | 2 | 2 | 2 | 2 | 0 | 2 | 2 | 2 | 2 | — | — | 8/9 |
| 34-36 | 2 | 2 | 2 | 2 | 0 | 1 | 0 | 0 | 2 | 0 | — | 5/10 |
| 31-44 | 2 | 2 | 2 | 2 | 0 | 1 | 2 | 2 | 1 | 0 | — | 6/10 |
| 25-33 | 2 | 2 | 1 | 2 | 2 | 0 | 0 | 2 | 1 | — | — | 5/9 |
| 25-71 | 2 | 2 | 2 | 2 | 0 | 2 | 1 | 2 | 1 | 2 | 2 | 8/11 |
| 62-40 | 2 | 1 | 2 | 2 | 0 | 1 | — | — | — | — | — | 3/6 |
| 63-28 | 2 | 2 | 0 | 2 | 0 | 0 | 2 | 2 | 0 | 0 | — | 5/10 |
| 63-36 | 2 | 2 | 0 | 2 | 1 | 2 | 0 | 2 | 2 | 2 | — | 7/10 |
| 63-14 | 2 | 2 | 2 | 2 | 0 | 1 | 2 | 0 | — | — | — | 5/8 |
| 63-49 | 2 | 2 | 0 | 2 | 2 | 1 | 0 | 1 | 2 | 1 | — | 5/10 |
| 62-34 | 2 | 2 | 0 | 2 | 1 | 2 | 1 | 1 | 1 | 0 | — | 4/10 |
| 61-16 | 2 | 2 | 1 | 2 | 0 | 2 | 0 | 2 | 2 | 0 | — | 6/10 |
| 62-24 | 2 | 1 | 2 | 2 | 2 | 2 | 0 | 1 | 0 | — | — | 5/9 |
| 56-13 | 2 | 2 | 2 | 2 | 1 | 2 | 2 | 2 | 1 | 0 | — | 7/10 |
| 54-26 | 2 | 2 | 2 | 2 | 0 | 0 | 2 | 2 | 0 | 0 | — | 6/10 |
| 54-28 | 2 | 2 | 2 | 2 | 2 | 1 | 2 | 0 | 1 | 2 | — | 7/10 |
| 54-04 | 2 | 2 | 2 | 1 | 2 | 2 | 0 | 2 | 0 | 0 | 2 | 7/11 |
| 1-141 | 2 | 2 | 2 | 1 | 0 | 0 | 1 | 0 | 0 | 2 | 0 | 4/11 |
| 2-16 | 2 | 2 | 2 | 0 | 1 | 0 | 0 | 0 | 1 | 0 | 1 | 3/11 |
| X | 2 | 2 | 0 | 2 | 2 | 1 | 2 | 2 | 1 | 0 | 2 | 7/11 |
| 31-01 | 2 | 2 | 1 | 1 | 2 | 2 | 1 | 1 | 2 | 1 | 1 | 5/11 |
| 17-114 | 2 | 2 | 2 | 1 | 1 | 0 | 2 | 0 | 0 | — | — | 4/9 |
| 46-16 | 2 | 2 | 2 | 2 | 0 | 0 | 0 | 0 | 0 | 2 | 1 | 5/11 |
| 39-05 | 2 | 2 | 2 | 2 | 1 | 1 | 0 | 2 | 0 | — | — | 5/9 |
| 37-09 | 2 | 2 | 2 | 1 | 0 | 1 | 1 | 0 | 0 | 1 | — | 3/10 |
| 37-08 | 2 | 2 | 2 | 2 | 2 | 1 | 0 | 1 | 0 | — | — | 5/9 |
| 58-22 | 2 | 1 | 2 | 2 | — | — | — | — | — | — | — | 3/4 |
| 68-17 | 2 | 2 | 2 | — | — | — | — | — | — | — | — | 3/3 |

[1]Score was based on a visual rating 0 to 3 compared to control. Six to eight replicate plants were used in each trial.

TABLE 3

SUMMARY OF GREENHOUSE ASSAYS FOR SELECTION OF SOYBEAN PGPR

| Strain | Score[1] per Trial No. | | | | | | | | Number of Trials with Score of 2 or 3/Total Number of Trials |
|---|---|---|---|---|---|---|---|---|---|
| | 1 | 2 | 3 | 4 | 5 | 6 | 7 | 8 | |
| GR25-25 | 2 | 2 | 2 | 2 | 2 | 2 | 1 | 2 | 7/8 |
| G25-46 | 2 | 2 | 0 | 0 | — | — | — | — | 2/4 |
| G23-28 | 2 | 0 | 0 | — | — | — | — | — | 1/3 |
| G23-34 | 2 | 0 | 2 | 2 | — | — | — | — | 3/4 |
| 67-04 | 2 | 2 | 2 | 1 | 2 | — | — | — | 4/5 |
| 66-05 | 2 | 0 | 2 | 0 | 2 | 2 | 2 | 2 | 6/8 |
| 55-14 | 2 | 2 | 2 | 0 | — | — | — | — | 3/4 |
| G2-52 | 2 | 1 | 2 | 0 | — | 1 | — | — | 2/4 |
| 57-10 | 2 | 0 | 2 | 0 | 2 | 0 | — | — | 3/6 |
| 58-42 | 2 | 2 | 2 | 1 | 2 | 2 | — | — | 4/6 |
| 58-21 | 2 | 0 | 2 | 2 | 1 | 0 | 2 | 2 | 6/8 |
| G1-05 | 2 | 2 | 0 | 2 | 2 | 1 | — | — | 4/6 |
| 62-10 | 2 | 2 | 1 | 1 | 0 | — | — | — | 2/6 |
| 62-19 | 2 | 0 | 2 | 0 | 0 | — | — | — | 2/5 |
| 61-03 | 2 | 1 | 1 | 2 | — | — | — | — | 2/4 |
| 61-06 | 2 | 0 | 0 | 2 | — | — | — | — | 2/4 |
| 61-09 | 2 | 2 | 0 | 2 | 2 | — | — | — | 4/5 |
| 61-24 | 2 | 1 | 0 | 2 | 0 | — | — | — | 2/5 |
| 61-08 | 2 | 1 | 0 | 2 | 2 | — | — | — | 3/5 |
| 61-10 | 2 | 0 | 2 | 0 | 0 | 2 | — | — | 3/6 |
| 56-20 | 2 | 2 | 1 | 1 | 2 | 1 | 2 | — | 4/7 |
| 55-13 | 2 | 2 | 0 | 2 | 2 | 2 | — | — | 5/6 |
| 2-67 | 2 | 2 | 0 | 0 | — | — | — | — | 2/4 |
| 17-76 | 2 | 2 | 0 | 1 | 1 | — | — | — | 2/5 |

[1]Root system development was visually ranked in comparison to controls on a scale of 0 to 3 with 8 replications.

EXAMPLE 3.

Field Tests Using Selected Rhizobacterial Strains.

Field trials were conducted using a total of 21 rapeseed PGPR strains and 14 soybean PGPR strains. A total of four soybean and four rapeseed trials were hand-planted using seed dipped into bacterial suspensions similar to those used for the greenhouse assays in Example 2. Two cultivars ("Maple Arrow" and "Evans") were used for the soybean tests, and one ("Tobin") for the rapeseed tests, as detailed in Tables 4 and 5, respectively. All trials were of the latin square design (8×8), with seven bacterial treatments and one control, all with eight replicate, 4 meter-long rows. Control seeds were dipped in 0.1M $MgSO_4$ prior to planting.

Data were collected on emergence by counting seedlings at a 1- to 2-day frequency from the time emergence began until the counts did not change. Vigor ratings were based, for soybean, on a visual rating (1 to 10) forty-six days after planting; for rapeseed, on a visual rating (1 to 10) twenty-five days after planting. Date of first flowering was recorded for each treatment/rep in all experiments. Plots were harvested at maturity, seed was collected and cleaned, and yield was determined based on 10% seed moisture. All collected data were analyzed for a significant test value using an analysis of variance. When a significant F value was detected, the treatment means were compared to control means using the "least significant difference" (LSD) value.

Figure 1B:
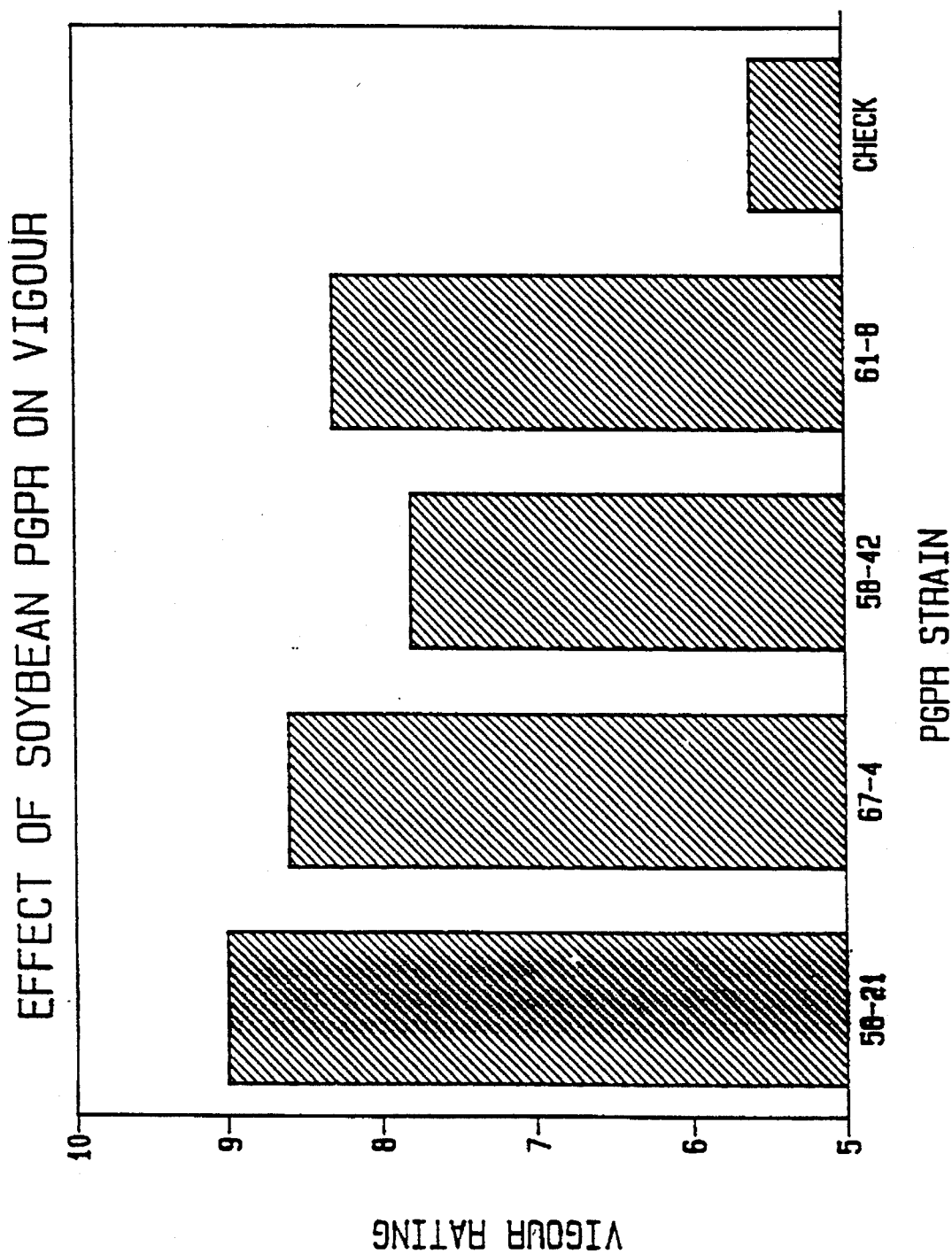
Figure 1C:
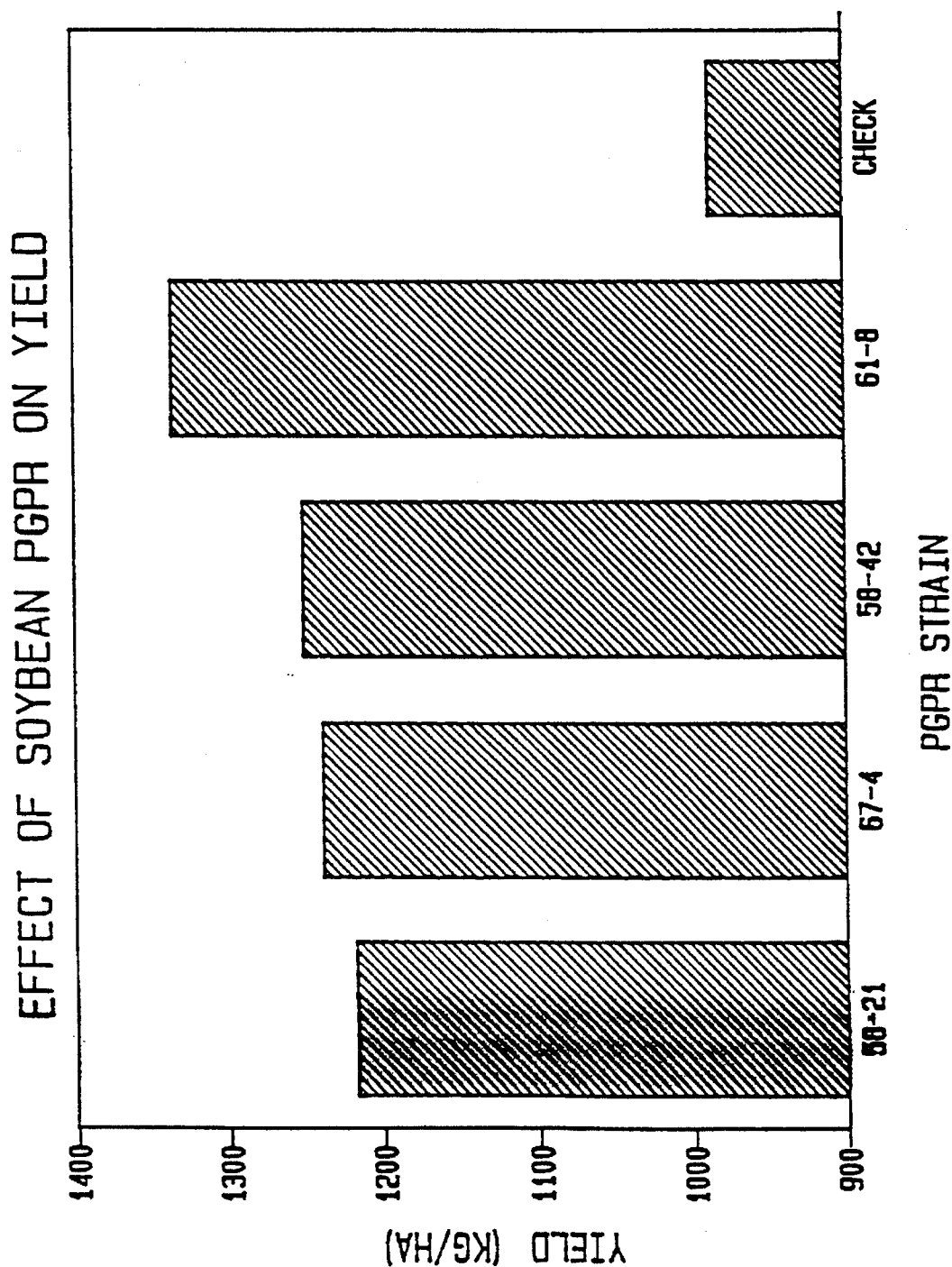

Ten of the tested strains induced significant increases in soybean yield, ranging from 13% to 35% relative to controls (see Table 4). The combined yield-increase figures for each PGPR strain in all soybean trials are shown in Table 6. As indicated there, nine of thirteen tested strains induced average yield increases of 10 to 23%. A few of the tested strains, such as 55-13A, exhibited a cultivar-specificity in yield enhancement. Four PGPR strains which increased yield of soybean also stimulated emergence rates and increased plant vigor compared to controls, as shown in FIG. 1A-C. No consistent effects of PGPR were observed on flowering date.

Figure 2A:
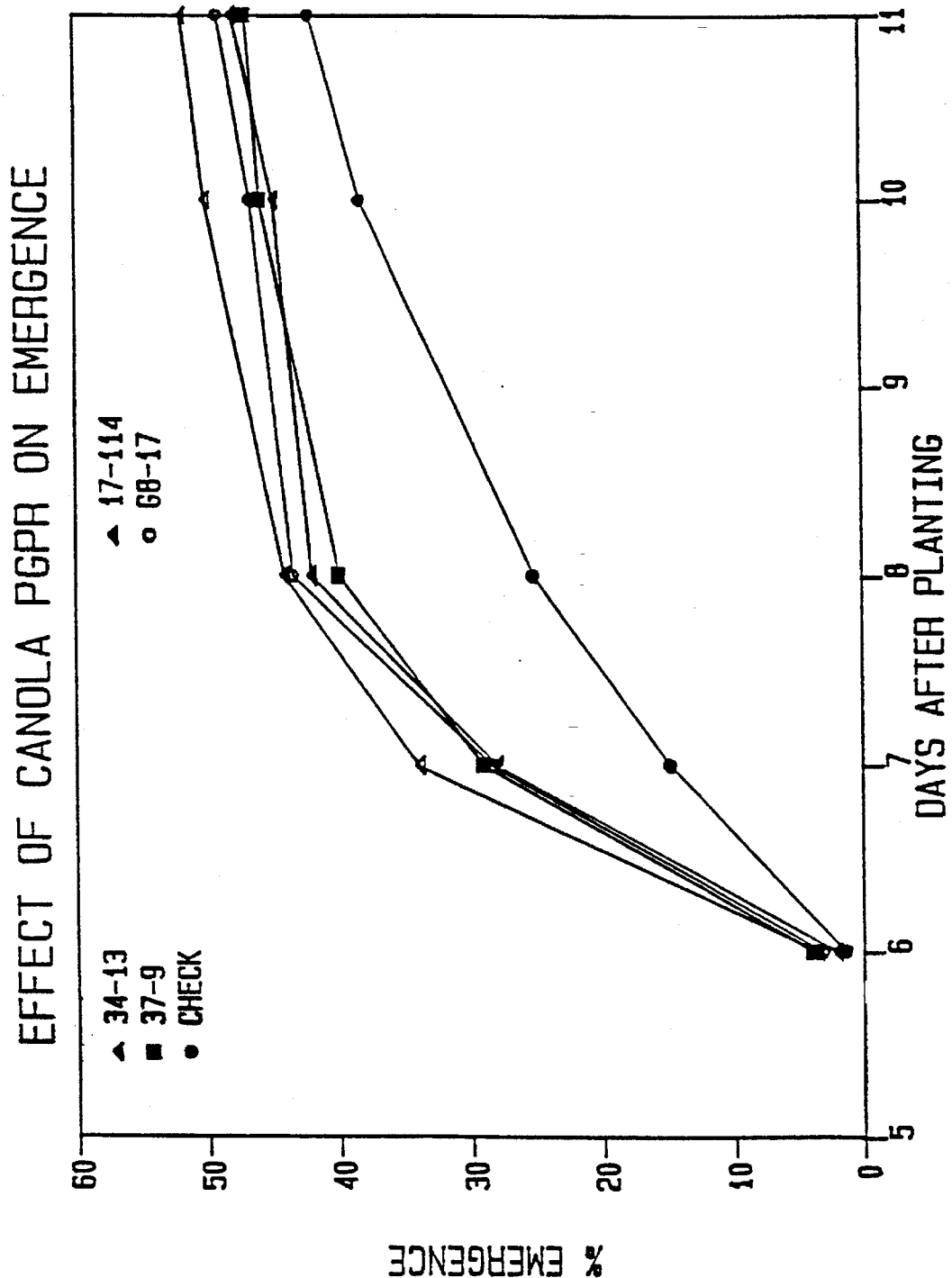
FIGS. 2A, 2B and 2C graphically depict the corresponding PGPR-mediated effects in rapeseed ("canola").
Figure 2B:
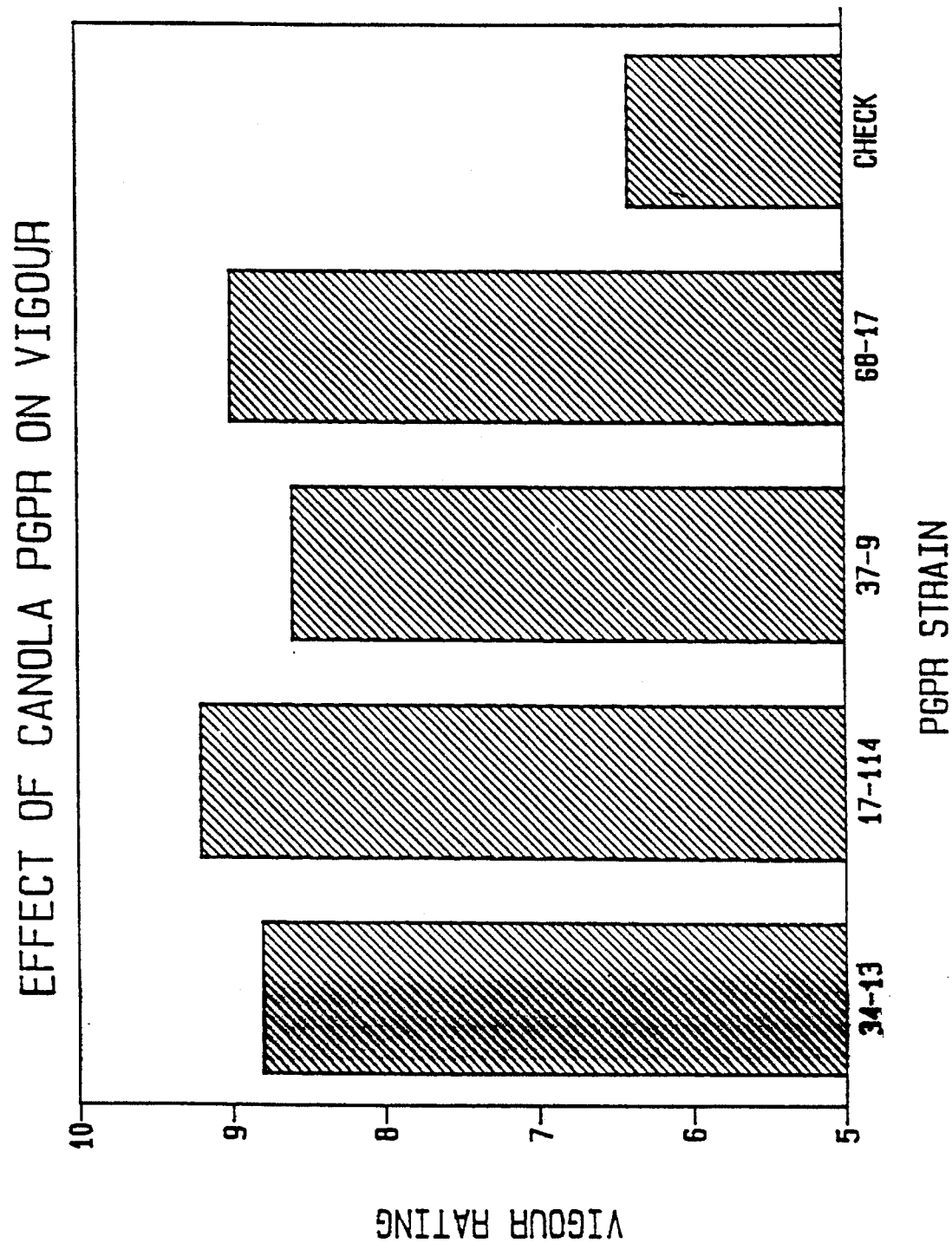
Figure 2C:
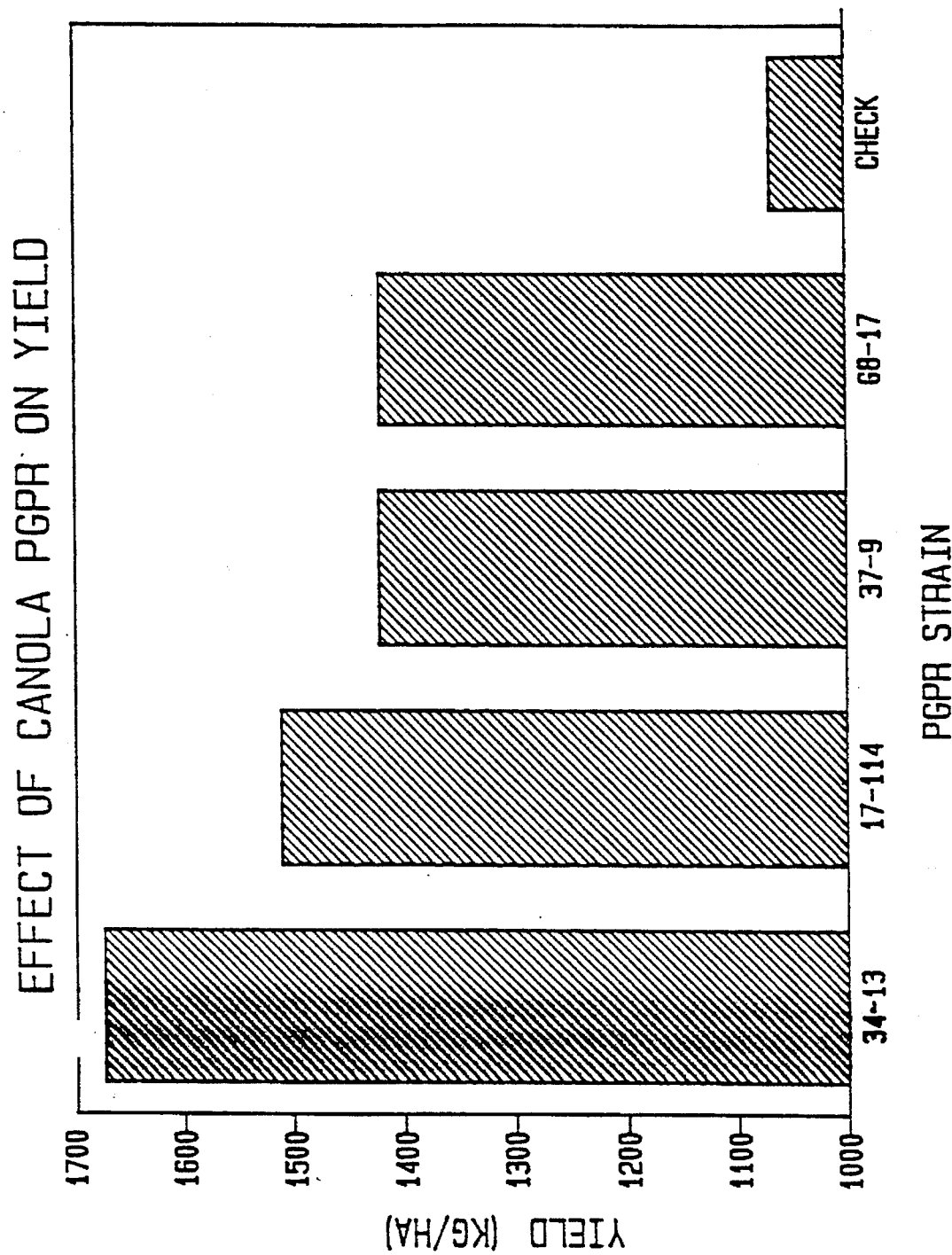

Thirteen of twenty-eight tested strains induced significant yield increases in rapeseed, ranging from 24 to 57% compared to controls (see Table 5). Approximately half of the 28 PGPR strains tested induced increases to emergence rates. Representative data for four strains are shown in FIG. 2A. Vigor of plants was significantly increased by 15 strains (Table 5 and FIG. 2B), 12 of which also induced significant yield increases.

TABLE 4

PGPR EFFECTS ON SOYBEAN VIGOR AND YIELD[1] (CALEDON, ONTARIO)

| Treatment | Cultivar 'Maple Arrow' | | | Cultivar 'Evans' | |
|---|---|---|---|---|---|
| | Vigor Rating[1] | Yield (kg/ha) | Percent Change From Control | Yield (kg/ha) | Percent Change From Control |
| 67-4 | 8.6** | 1237 | 25** | 1483 | 17* |
| 58-42 | 7.8** | 1250 | 27** | 1511 | 19** |
| 61-8 | 8.3** | 1336 | 35** | 1405 | 11 |
| G1-5 | 8.0** | 1148 | 16* | 1316 | 4 |
| 58-21 | 9.0** | 1217 | 23** | 1371 | 8 |
| 55-14 | 8.1** | 1201 | 22** | 1411 | 11 |
| 61-9A | 7.4** | 1059 | 7 | 1355 | 7 |
| Control | 5.6 | 987 | — | 1266 | — |
| 55-13A | 6.4 | 1041 | 16 | 1356 | −2 |
| G25-25 | 7.3 | 1036 | 16 | 1580 | 14* |
| G2-52 | 7.6 | 1033 | 15 | 1556 | 13* |
| 56-20 | 7.3 | 938 | 5 | 1478 | 7 |
| 55-13B | 7.0 | 937 | 5 | 1550 | 12 |
| G23-34 | 6.7 | 836 | −7 | 1487 | 8 |
| 57-10 | 6.7 | 829 | −7 | 1772 | 28** |
| Control | 6.3 | 895 | — | 1382 | — |

[1]All numbers are means of 8 replications
[2]Vigour was based on a visual rating of 1 to 10 and was taken 46 days after planting
*, **Significant increase compared to control at P = 0.10, 0.05

TABLE 5

PGPR EFFECTS ON RAPESEED VIGOR AND YIELD[1] (CALEDON, ONTARIO)

| Treatment | Vigor Rating[2] | Yield (kg/ha) | Percent Change From Control Yield |
|---|---|---|---|
| 31-12 | 9.1** | 1208 | 42** |
| 44-9 | 8.6* | 1105 | 30* |
| 31-44 | 7.9 | 1099 | 29* |
| 31-34 | 7.9 | 1030 | 21 |
| 25-33 | 8.2 | 941 | 10 |
| 24-36 | 8.1 | 934 | 10 |
| Control | 7.7 | 849 | — |
| G3-9 | 7.9 | 822 | 3 |
| 63-49 | 9.2* | 1382 | 41** |
| 63-14 | 9.1* | 1226 | 25* |
| 63-28 | 9.6** | 1173 | 19 |
| 25-71 | 8.6 | 1132 | 15 |
| 61-16 | 8.6 | 1119 | 14 |
| 63-36 | 8.0 | 1083 | 10 |
| 62-34 | 8.4 | 1078 | 9 |
| Control | 8.3 | 982 | — |
| 56-13 | 8.8* | 1380 | 24* |
| X | 8.3 | 1313 | 17 |
| 2-16 | 8.8* | 1301 | 16 |
| 54-4 | 9.1** | 1252 | 12 |
| 1-141 | 8.1 | 1165 | 4 |

TABLE 5-continued

PGPR EFFECTS ON RAPESEED VIGOR AND YIELD[1]
(CALEDON, ONTARIO)

| Treatment | Vigor Rating[2] | Yield (kg/ha) | Percent Change From Control Yield |
|---|---|---|---|
| 62-24 | 7.8 | 1161 | 4 |
| Control | 8.1 | 1117 | — |
| 54-26 | 8.0 | 1114 | 0 |
| 34-13 | 9.4** | 1674 | 57** |
| 17-114 | 9.6** | 1512 | 41** |
| 37-93 | 9.3* | 1423 | 33* |
| G8-17 | 9.5** | 1422 | 33* |
| 39-8 | 9.6** | 1420 | 33* |
| 46-8 | 9.3* | 1410 | 32* |
| 37-8 | 9.6** | 1382 | 29* |
| Control | 8.2 | 1069 | — |

[1]All values are mean of 8 replications
[2]Vigor rating is on a scale of 1 to 10 as measured 25 days after planting
*Significant at $P = 0.10$
**Significant at $P = 0.05$

TABLE 6

SUMMARY OF SOYBEAN YIELD INCREASES BY PGPR[1]

| Treatment | "Maple Arrow" | "Evans" | Overall Mean of % Change |
|---|---|---|---|
| 55-14 | 22 | 11 | 17 |
| G23-34 | −7 | 8 | 1 |
| 58-42 | 27 | 19 | 23 |
| G1-5 | 16 | 4 | 10 |
| 55-13A | 16 | −2 | 7 |
| G2-52 | 15 | 13 | 14 |
| 58-21 | 23 | 8 | 16 |
| 61-9A | 7 | 7 | 7 |
| 61-8 | 35 | 11 | 23 |
| 56-20 | 5 | 7 | 6 |
| 67-4 | 25 | 17 | 21 |
| 57-10 | −7 | 28 | 11 |
| 55-13B | 5 | 12 | 9 |
| G25-25 | 16 | 14 | 15 |

[1]Values shown are the percentage increases compared to solution-treated controls.

What is claimed is:

1. A bacterial culture consisting essentially of at least one rhizobacterial strain that increases the yield of an agronomic, nonroot crop selected from the group consisting of cereal, oilseed, legume and maize, wherein said strain has substantially all of the crop yield increase characteristics of *Pseudomonas putida* 55-14, deposited under ATCC accession No. 53,530, and variants thereof, wherein said variants retain sasid chracteristics.

2. A bacterial culture according to claim 1, wherein said strain increases yield in soybean, flax or rapeseed plants.

3. A bacterial culture according to claim 2, wherein said strain increases yield in rapeseed plants grown from seed exposed to said strain by up to about 57%, relative to rapeseed plants grown from seed not exposed to said strain.

4. A bacterial culture according to claim 5, wherein said strain increases said yield by an amount ranging between about 24% and 57%.

5. A bacterial culture according to claim 5, wherein said rapeseed plants grown from seed exposed to said strain have average yields increased by at least about 10%.

6. A bacterial culture according to claim 1, wherein said strain increases yield in soybean plants grown from seed exposed to said strain by up to about 37%, relative to soybean plants grown from seed not exposed to said strain.

7. A bacterial culture according to claim 6, wherein said soybean plants grown from seed exposed to said strain have average yields increased by about to 23%.

8. A bacterial culture according to claim 1, wherein said strain increases yield in plants selected from the group consisting of wheat, barley, oats, sorghum, rye, millet and rice.

9. A bacterial culture according to claim 1, wherein said strain increases yield in maize plants.

10. A bacterial culture according to claim 1, wherein said strain also increases vigor and/or emergence rate in said plants.

11. A bacterial culture according to claim 1, wherein said strain is a fluorescent pseudomonad.

12. A bacterial culture according to claim 1, wherein said strain is of a species selected from the group consisting of *Pseudomonas putida*, *Pseudomonas fluorescens*, *Arthrobacter citreus* and *Serratia liquefaciens* and Flavobacterium sp.

13. A bacterial culture according to claim 1, wherein said nonroot crop is grown from seed treated in an aqueous suspension of said strain.

14. A bacterial culture according to claim 1, wherein said strain is a free-living rhizobacterial strain.

15. A composition of matter composing (i) a biologically pure bacterial culture of a rhizobacterial strain that increases yield of an agronomic, nonroot crop selected from the group consisting of disease-free cereal, oilseed, legume and maize plants and (ii) an agriculturally-compatible carrier, wherein said strain has substantially all of the increased crop yield characteristics of *Pseudomonas putida* 55-14, deposited under ATCC accession No. 53,530, and variants thereof, wherein said variants retain said characteristics.

16. A composition according to claim 15, wherein said strain increases yield in soybean, flax or rapeseed plants.

17. A composition according to claim 16, wherein said strain increases yield in soybean plants grown from seed exposed to said strain by up to about 37%, relative to soybean plants grown from seed not exposed to said strain.

18. A composition according to claim 17, wherein said soybean plants grown from seed exposed to said strain have average yields increased by about 10 to 23%.

19. A composition according to claim 16, wherein said strain increases yield in rapeseed plants grown from seed exposed to said strain by up to about 57%, relative to rapeseed plants grown from seed not exposed to said strain.

20. A composition according to claim 19, wherein said strain increases said yield by an amount ranging between about 24% and 57%.

21. A composition according to claim 19, wherein said rapeseed plants grown from seed exposed to said strain have average yields increased by at least about 10%.

22. A composition according to claim 15, wherein said strain increases yield in plants selected from the group consisting of wheat, barley, oats and rice.

23. A composition according to claim 15, wherein said strain increases yield in maize plants.

24. A composition according to claim 15, consisting essentially of said strain and said carrier.

25. A composition according to claim 15, wherein said strain also increases vigor and/or emergence rate in said plants.

26. A composition according to claim 15, wherein said strain is a fluorescent pseudomonad.

27. A composition according to claim 15, wherein said strain is of a species selected from the group consisting of *Pseudomonas putida*, *Pseudomonas fluorescens*, *Arthrobacter citreus*, *Serratia liquefaciens* and Flavobacterium sp.

28. A composition according to claim 15, wherein bacterial cells of said strain are suspended in a carrier which comprises a liquid.

29. A composition according to claim 28, wherein said carrier is an aqueous liquid.

30. A composition according to claim 29, further comprising an alginate.

31. A composition according to claim 30, further comprising an agriculturally compatible oil, such that said composition is an emulsion containing bacterial cells of said strain.

32. A composition according to claim 28, wherein said carrier comprises an agriculturally compatible oil.

33. A composition according to claim 32, further comprising a gum in an amount such that said composition is an emulsion in which said bacterial cells of said strain are dispersed.

34. A composition according to claim 28, wherein said carrier further comprises a granular material onto which said liquid is absorbed.

35. A composition according to claim 34, wherein said granular material comprises pelleted peat or perlite granules.

36. A composition according to claim 15, wherein said composition is the product of a process comprising the steps of (a) dispersing bacterial cells of said strain in an aqueous slurry and (b) drying said slurry to powder at a temperature which does not adversely affect said cells.

37. A composition according to claim 36, wherein said process further comprises the step of mixing said powder in an agriculturally compatible oil.

38. A composition according to claim 36, wherein said process further comprises the step of mixing said powder with material selected from peat, talc and diatomaceous earth.

39. A composition according to claim 15, wherein said strain is a free-living rhizobacterial strain.

40. An inoculated seed product produced by a process comprising the steps of (i) bringing a seed into contact with a composition as recited in claim 15, and (ii) inoculating the seed with the composition to produced the inoculated seed product.

41. A biologically pure bacterial culture of a rhizobacterial strain that increases seed production of disease-free agronomic, non-root crops selected from the group consisting of cereal, oilseed, legume and maize, wherein said strain has substantially all of the crop yield increase characteristics of *Pseudomonas putida* 55-14, deposited under ATCC accession No. 53,530, and variants thereof, wherein said variants retain said characteristics.

42. A method for obtaining a strain that increases yield in disease-free cereal, oilseed, legume or maize crops, comprising the steps of:

testing bacterial strains for their ability to colonize roots to obtain a strain that is root-colonizing;

assessing the ability of the root-colonizing bacterial strain to promote yield of agronomic, nonroot crops selected from the group consisting of disease-free cereal, oilseed, legume and maize plants by applying the root-colonizing bacterial strain under field conditions to the growth environment of the plant, wherein said strain has substantially all of the increased crop yield characteristics of *Pseudomonas putida* 55-14, deposited under ATCC accession No. 53,530, and variants thereof, wherein said variants retain said characteristics, and maintaining a culture of the root-colonizing bacterial strain if it promotes the yield of the plant.

43. A method according to claim 42, wherein the root-colonizing bacterial strain is additionally tested under greenhouse conditions for its ability to promote growth of a plant selected from the group of disease-free cereal, oilseed, legume and maize plants before it is applied under field conditions to assess its ability to promote yield of the plant.

44. A method according to claim 42, wherein the bacterial strains to be tested for root-colonizing ability are isolated from soil.

45. A method according to claim 42, wherein the step of assessing the ability of the root-colonizing bacterial strain to promote yield under field conditions comprises applying the root-colonizing bacterial strain to a seed of the plant and planting the seed.

46. A biologically pure bacterial culture of a rhizobacterial strain selected from the group consisting of *Pseudomonas putida, Pseudomonas fluorescens, Arthrobacter Citreus,* and *Serratia liquifaciens,* and Flavobacterium sp. that increases yield in disease free cereal, oilseed, legume or maize plants that is identified according to the method recited in claim 42.

\* \* \* \* \*